(12) United States Patent
Rousseau

(10) Patent No.: US 6,767,511 B1
(45) Date of Patent: Jul. 27, 2004

(54) AUTOMATIC ANALYSIS APPARATUS USED FOR TIMING BLOOD COAGULATION

(75) Inventor: Alain Rousseau, Paris (FR)

(73) Assignee: Junior Instruments (FR)

( * ) Notice: Subject to any disclaimer, the term of this patent is extended or adjusted under 35 U.S.C. 154(b) by 0 days.

(21) Appl. No.: 09/719,091

(22) PCT Filed: May 6, 1999

(86) PCT No.: PCT/FR99/01082

§ 371 (c)(1),
(2), (4) Date: Apr. 16, 2001

(87) PCT Pub. No.: WO99/64839

PCT Pub. Date: Dec. 16, 1999

(30) Foreign Application Priority Data

Jun. 10, 1998 (FR) .............................. 98 07484

(51) Int. Cl.$^7$ .............................................. G01N 33/48
(52) U.S. Cl. .......................... 422/73; 422/68.1; 422/62; 436/43; 436/69; 436/164
(58) Field of Search ............................... 422/62, 64, 65, 422/68.1, 73; 436/43, 44, 48, 49, 69, 164

(56) References Cited

U.S. PATENT DOCUMENTS

| | | | | |
|---|---|---|---|---|
| 4,918,984 A | * | 4/1990 | Martinoli et al. | ........... 73/64.43 |
| 5,316,726 A | * | 5/1994 | Babson et al. | ................ 422/65 |
| 5,885,529 A | * | 3/1999 | Babson et al. | ................ 422/65 |

* cited by examiner

Primary Examiner—Lyle A. Alexander
(74) Attorney, Agent, or Firm—William A. Drucker

(57) ABSTRACT

The invention concerns an automatic analysis apparatus wherein the liquid sample to be analysed is arranged in a cup (C) containing a ferromagnetic ball (BE) driven in a periodic motion under the effect of a magnetic field. In order to detect the ball (BE) movements representing the physical state of the sample, an electronic camera (CM$_1$ to CM$_3$) is oriented towards the cup (C) while a processor (P) determines, from the cup (C) image, the modifications in the ball (BE) movements. The invention is useful for producing small-size and medium-size automatic appliances.

8 Claims, 2 Drawing Sheets

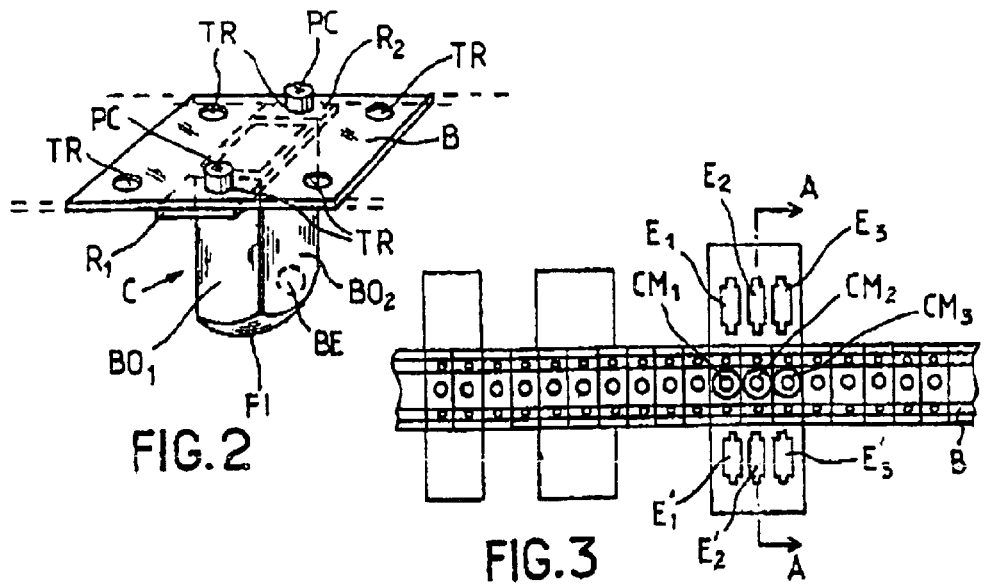
FIG.2
FIG.3
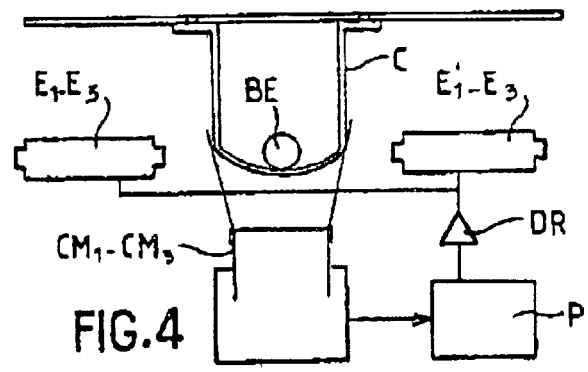
FIG.4
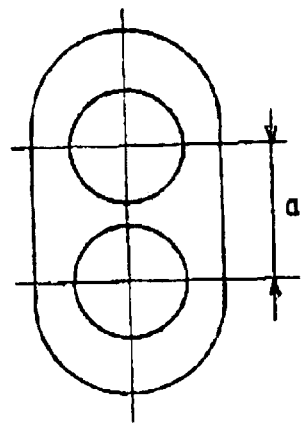
FIG.5
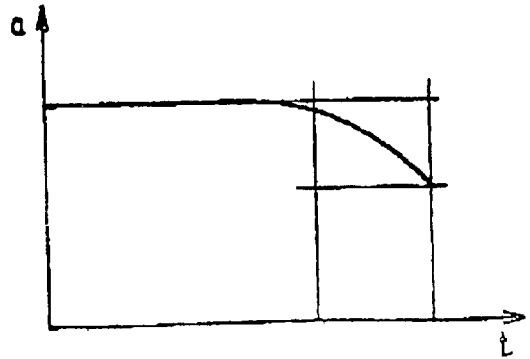
FIG.6

AUTOMATIC ANALYSIS APPARATUS USED FOR TIMING BLOOD COAGULATION

BACKGROUND OF THE INVENTION

The present invention concerns an automatic analysis apparatus used for determining times for modifying the physical state of a fluid medium.

It applies particularly, but not exclusively, for determining timing blood coagulation in accordance with a method wherein the blood sample is arranged at the bottom of a cup containing a ferromagnetic ball driven in a periodic motion under the effect of an external magnetic field. The modifications of the movements of the ferromagnetic ball (for example the amplitude and/or frequency variations) representative of changes of the physical state of the blood are then detected with the aid of suitable means (optoelectronics—inductive, capacitive, densitometric).

The principle of this detection is given in detail in the European patent No EP 88403279.8 filed in the name of the company SERBIO S.A.

DESCRIPTION OF THE PRIOR

IN an analysis apparatus of this type with a high rate (about 360 tests/hour), each cup for single usage has the shape of a small parallelepiped whose incurved bottom constitutes the rolling path of the ball, whereas the face opposite the bottom has an opening. These cups are arranged side by side and fixed so as to be detached from a flexible support strip which temporarily blocks off their openings. The strip equipped with cups can be wound onto a coil able to be engaged on a device provided in a storage and distribution compartment of a robot.

In this type of automatic machines whose failure rate, in all cases, is about 3 interventions/year, the cups are extracted from the strip so as to be then arranged in suitable locations inside the robot. Thus, these machines and sources of failures include relatively complex and expensive transfer and grasping means. They are suitable for laboratories having a large number of tests to be carried out in keeping with the previously mentioned rates and possessing a culture and special skills in the laboratory robots.

At the same time, there are available for use in small laboratories not having special skills in robots manual or semi-automatic machines having good reliability (intervention rate subsequent to failures, in all cases, of about 1 intervention/10 years).

Between the two types of devices previously mentioned, there is a gap to be filled corresponding to small ands average-sized automatic machines able to function at rates of between 60 and 120 tests/hour and of necessity possessing good reliability on account of the structure and skill of the laboratories for which these machines are intended.

The patent EP 0 525 273 A1 also concerns a device for determining blood coagulation time and introducing a plate on which a plurality of cavities are arranged in which balls are placed with the samples. This plate is subjected to a circular movement under the effect of a motor.

According to this document, an electronic camera takes a picture of the plate with all its cavities so as to detect ball movement variations.

However, the complexity of the solutions used for automation and its corresponding costs constitutes a drawback in small and medium-sized laboratories. First of all, this complexity is mainly due to handlings of the cups required in the analysis cycle for picking up said cups, detach them from the film, bring them into the measuring chamber and for extracting them following measurement with a view to discharging them into a discharge compartment, it being understood that these handlings have to be carried out owing to the nature of the means used for determining the blood coagulation time.

OBJECT OF THE INVENTION

Thus, the aim of the invention is to embody an apparatus less expensive and having a simpler design than known devices, but which permits sufficient rates so as to be able to form part of the field of small and medium-sized devices. To this effect, the invention concerns an automatic analysis apparatus of the type in which a liquid sample to be analysed is arranged in a cup containing a ferromagnetic ball driven in a periodic movement under the effect of a magnetic field, this apparatus including an electronic camera orientated towards the cup, and a processor for detecting from the image of the cup the modifications of the movements of the ball.

SUMMARY OF THE INVENTION

According to the invention, this apparatus is characterised in that it uses a plurality of cups secured to a support strip moving past one by one in a detection station, and in that the detection station includes at last one electronic camera situated below the cups, and electromagnetic means placed laterally with respect to the strip at the right of the side faces of the cups so as to generate a magnetic field inside the movement axis of the ball contained in the cup located in the detection station, the running off movement of the strip able to be of the step-by-step or even continuous type.

Advantageously, the electronic camera shall be placed below the cup, the electromagnetic means for generating the external magnetic field then being arranged laterally inside the movement axis of the ball.

This association of camera and electromagnetic means is particularly suitable for the line detection of the movements of the balls contained in the cups.

In this case, the cups which remain fixed on the flexible support strip, are driven according to a step-by-step movement, indeed possibly continuous, along a path passing successively through a pipette station in which a reactive product is injected, a detection station including electromagnetic means placed laterally on either side of the strip, and at least one electronic camera placed under the path of the cups in the emission zone of the magnetic field, and a station for storing the used cups.

The pipette station could advantageously include a mobile pipette, both vertically and along a horizontal circular path so as to be able to occupy an injection position situated at the right of the path of the cups so as to allow reagents to be injected inside the latter, a rinsing position situated at the right of a rinsing cup and at least one reactive agent sampling position situated at the right of a sampling area of a reactive agent distributor.

This reactive agent distributor could consist of a carrousel including a plurality of cups of mobile reactive agents along a circular path so as to be able to be brought successively into the sampling area.

There now follows a description of one embodiment of the invention given by way of non-restrictive examples with reference to the accompanying drawings on which:

BRIEF DESCRIPTION OF THE DRAWINGS

FIG. 2 is a diagrammatic perspective view of a cup mounted on its strip;

FIG. 3 is a top diagrammatic view of the strip equipped with its cups when it passes through the incision, pipette and detection stations;

FIG. 4 is a vertical diagrammatic section along A/A of FIG. 3;

FIG. 5 is a view in a form of a diagram showing the movements of the ball contained in a cup inside the field of a camera;

FIG. 6 is a graph showing the amplitude of the movements of the ball according to the time.

DESCRIPTION OF THE PREFERRED EMBODIMENTS

Figure 1:
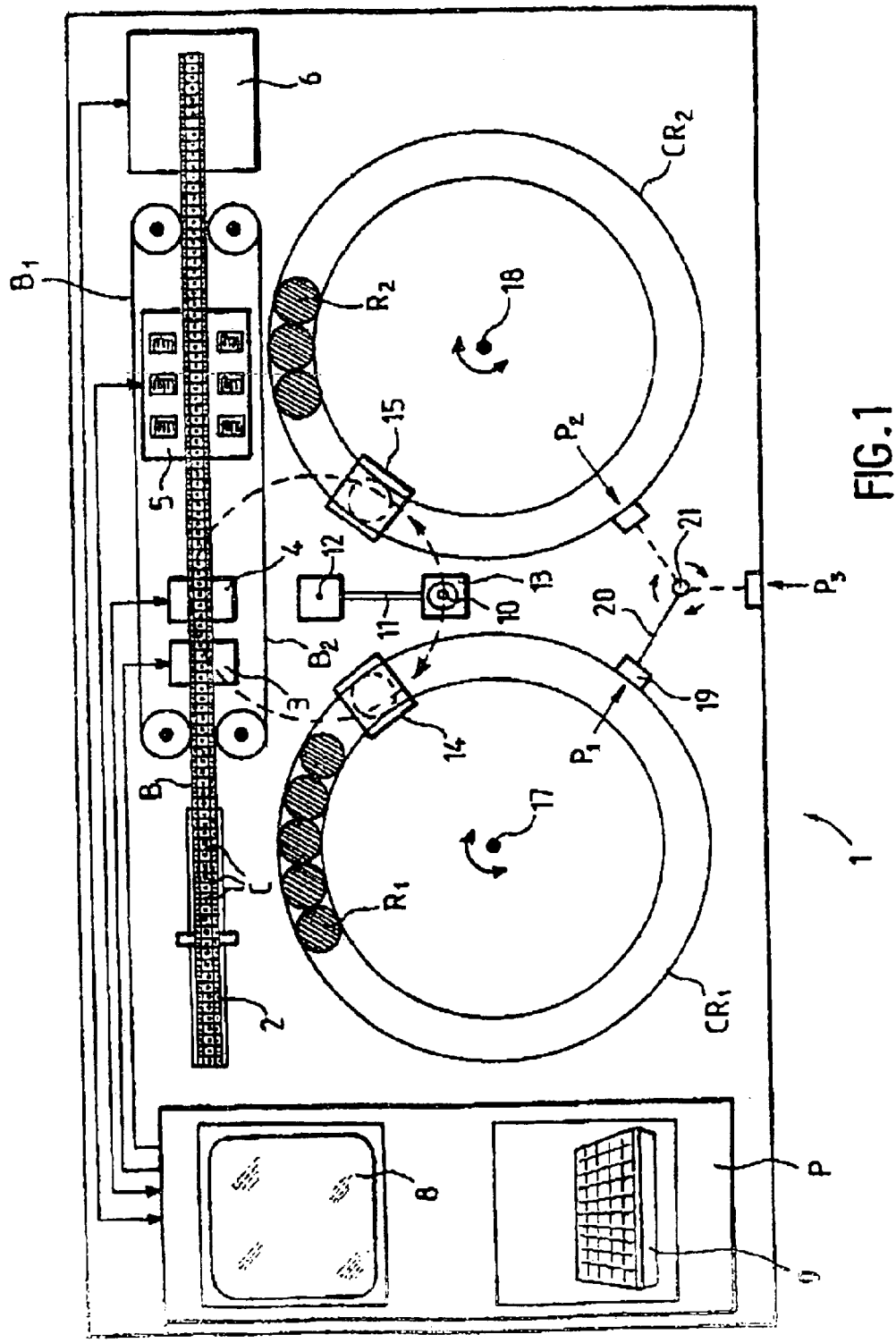
FIG. 1 diagrammatically represents an average-sized automatic analysis apparatus.

In this example, the automatic analysis apparatus 1 introduces a feed to the cups comprising a coil 2 on which a strip B, carrying a plurality of cups C, is wound.

As shown on FIG. 2, the cups C embodied by the moulding of a transparent plastic material, each having a flat parallelepiped body whose incurved bottom FI constitutes a rolling path for a ferromagnetic ball BE. Opposite this bottom FI, the cup C has an opening at the level of which its two opposing edges $BO_1$, $BO_2$ are extended at a right angle by two respective shoulders $R_1$, $R_2$ each fitted with a cylindrical protuberance PC extending from the side opposite the body. These two protuberances are intended to be forcefully engaged inside two respective holes TR respectively provided on the two side borders of the strip B.

The coil 2 is mounted rotating inside a receptacle so as to allow the strip B to be unwound along a rectilinear path passing successively through an incision station 3 of the strip B (in a case where the strip has not already been pre-incised), a pipette station 4, a detection station 5, and then a recovery station 6 of the strip B provided with used cups.

The functioning of these various stations is managed by a processor P comprising a central unit and peripheral units, such as a screen 8/keyboard 9 unit.

The driving of the strip B along its path is ensured with the aid of a step-by-step drive mechanism introducing two endless strips $B_1$, $B_2$ guided by rollers and taking support on the side faces of the cups C borne by the strip B.

The pipette station 4 is served by an automated vertical pipette 10 able to move upwards so as to be able to take up a bottom pipette or rinsing position and an upper position allowing its movements inside a horizontal plane.

This pipette 10 is fixed to one of the extremities of an arm 11 mounted rotating by its other extremity around a vertical spindle 12. The driving in rotation of the arm 11 is ensured by a servomotor controlled by the processor P.

By means of this simple mechanism, the pipette 10 can be brought successively to the pipette area of the pipette station 4, a diametrical rinsing area 13 equipped with one or several rinsing cups, and two sampling areas 14, 15 arranged symmetrically with respect to the axis passing through the pipette area 4 and the rinsing area 13.

The sampling areas 14, 15 are situated inside the path of the receptacles $R_1$, $R_2$ carried by two respective carrousels $CR_1$, $CR_2$ rotary mobile around two vertical spindles 17, 18 and controlled by two servomotors controlled by the processor P.

One of these carrousels $CR_1$ is sued to contain the receptacles $R_1$ of blood samples to be analysed whereas the other $CR_2$ contains the receptacles $R_2$ allocated to the various reactive agents able to be used as part of the analyses to be carried out.

Of course, the processor P is programmed so as to control the pipette sequences appropriate to the nature of the analyses to be carried out and possibly successively including:

a prior rinsing of the pipette 10, the sampling of a dose of samples contained in one of the receptacles $R_1$ of the carrousel $CR_1$, the injection of this dose into a cup C situated on the pipette station 4, the rinsing of the pipette 10, the taking of a dose of the reactive agent contained in one of the receptacles $R_2$ of the carrousel $CR_2$, the injection of this reactive agent dose into the cup C, the identification of the blood samples to be analysed, as well as that of the reactive agents being made automatically by means of a bar code reader 19 able to read the bar codes present on the receptacles $R_1$, $R_2$ borne by the carrousels $CR_1$, $CR_2$.

In this example, for these readings, a single bar code reader 19 is used mounted at the extremity of an arm 20 pivoting around a vertical spindle 21 so as to be able to occupy three positions, namely:

a bar code reading position $P_1$ of the receptacles $R_1$ of the carrousel $CR_1$, a bar code reading position $P_2$ of the receptacles $R_2$ of the carrousel $CR_2$, and a position $P_3$ for reading the receptacles placed by the operator in a reading station, for example for picking up the information exploited by the processor as part of the functioning of the device.

The measuring station 4 here includes three successive measuring units each including (FIGS. 3 and 4):

a pair of coaxial electromagnets $E_1$, $E'_1$–$E_2$, $E'_2$–$E_3$, $E'_3$ situated on both sides of the strip B at the right of the side faces of the cups C, and an electronic camera $CM_1$, $CM_3$ whose lens is situated below the cups C borne by the strip B.

The electromagnets $E_1$, $E'_1$–$E_2$, $E'_2$–$E_3$, $E'_3$ are excited by a power circuit PR controlled by the processor P so as to generate a pulse magnetic field able to drive the ball BE according to an alternative movement at the bottom of the cup C.

The camera $CM_1$–$CM_3$ is coupled to the processor P which analyses in real time the image by means of an appropriate software so as to measure the amplitude a of the oscillations of the ball BE and determine the critical moment when this amplitude (FIGS. 5 and 6).

Of course, the processor P counts the time between the moment when the reactive agent has been injected into the cup C and this critical moment so as to deduce from it a coagulation time.

The use of several measuring units spread out on the path of the strip B has the advantage of allowing greater flexibility concerning operation and in particular considerably extending the range of the coagulation times of the blood samples to be analysed.

Of course, the step-by-step movements of the strip are synchronised with the operating times of each of the stations of the device and in particular with the magnetic field pulses generated by the coils.

The pipette station could possibly be situated at the same location as the measuring station.

Of course, the invention is not limited to the embodiment previously described.

Thus, for example, each camera could have a field including several cups each excited by a separate pair of electromagnets so as to follow the cup over a forward distance of several steps with a processor P programmed so as to simultaneously detect the movements of the balls of the various cups.

What is claimed is:

1. Automatic analysis apparatus of the type in which liquid samples to be analysed are placed in respective transparent cups of an assembly of cups disposed side by side and fixed on a strip, said cups each comprising a flat parallelepiped body having two parallel main faces, two opposite side faces, aN incurved bottom which constitutes a rolling path for a ferromagnetic ball inserted into said cup, an opening located opposite to said bottom and two opposite shoulders extending outwardly from two opposites sides of said opening, said shoulders being provided with means for removably fixing said cups on said strips with said main faces extending perpendicularly to the longitudinal axis of the strip, said apparatus further having a means for driving said strip and a station wherein said cups are introduced one by one by said strips, said station comprising means for injecting a reactive agent into said cup through said opening, electromagnetic means placed laterally with respect to the strip and therefore in front of the side faces of one of said cups present in said station, so AS to generate a magnetic field parallel to the main faces of said cup and to drive the ferromagnetic ball contained in this cup in a periodic movement along the rolling path of said cup, at least one electronic camera located below the bottom of said cup and coupled to a processor which comprises means for analysing in real time AN image produced by the camera, for measuring the amplitude of the oscillations of the ball present in said image and for determining the initial moment when this amplitude lowers below specific threshold.

2. Apparatus according to claim 1, wherein in said station the strip follows a rectilinear path passing successively through a pipette station, a detection station and a recovery station of the strip provided with its used cups.

3. Apparatus according to claim 1, wherein the pipette station is served by a vertical pipette able to move upwards and fixed to one of the extremities of an arm mounted rotating around a vertical spindle so as to be able to be brought by successively rotating to a pipette station, a rinsing station and to two sampling areas.

4. Apparatus according to claim 3, wherein the sampling areas are situated on the path of the receptacles borne by two respective carrousels able to move in rotation around two vertical spindles controlled by two servomotors, one of the carrousels being used to contain the blood samples receptacles, whereas the other contains the receptacles allocated to the reactive agents able to be used as part of the analyses it is desired to be carried out.

5. Apparatus according to claim 4, wherein said processor is programmed so as to control pipette sequences successively comprising:

a prior rinsing of the pipette, the taking of a dose of samples contained in one of the receptacles of the carrousel, the injection of this dose into a cup situated on the pipette station, the rinsing of the pipette, the taking of a dose of the reactive agent contained in one of the receptacles of the carrousel, the injection of this reactive agent dose into the cup.

6. Apparatus according to claim 5, wherein the blood samples to be analysed and the reactive agents are identified automatically by means of a bar code reader able to read the bar codes present on the receptacles borne by the carrousels.

7. Apparatus according to claim 6, which includes a single bar code reader mounted at the extremity of an arm pivoting around a vertical spindle so as to be able to occupy three positions, namely:

a position for reading the bar codes of the receptacles of the carrousel, a position for reading bar codes of the receptacles of the carrousel, and a position for reading receptacles placed by the operator in a reading station, for picking up information exploited by the processor as part of the functioning of the apparatus.

8. Apparatus according to claim 1, wherein the field of the camera includes several cups each excited by separate electromagnetic means and wherein the processor is programmed so as to simultaneously detect the movements of the balls of said cups.

* * * * *